US011871998B2

(12) United States Patent
Hornecker et al.

(10) Patent No.: US 11,871,998 B2
(45) Date of Patent: Jan. 16, 2024

(54) GRAVITY BASED PATIENT IMAGE ORIENTATION DETECTION

(71) Applicant: Stryker European Operations Limited, Carrigtwohill (IE)

(72) Inventors: Patrick Hornecker, Eichstetten (DE); Michael Mantke, Freiburg (DE)

(73) Assignee: Stryker European Operations Limited, Carrigtwohill (IE)

( * ) Notice: Subject to any disclaimer, the term of this patent is extended or adjusted under 35 U.S.C. 154(b) by 496 days.

(21) Appl. No.: 16/706,138

(22) Filed: Dec. 6, 2019

(65) Prior Publication Data

US 2021/0169577 A1 Jun. 10, 2021

(51) Int. Cl.
*A61B 34/20* (2016.01)
*A61B 6/00* (2006.01)
(Continued)

(52) U.S. Cl.
CPC ............. *A61B 34/20* (2016.02); *A61B 6/463* (2013.01); *A61B 6/547* (2013.01); *A61B 6/582* (2013.01);
(Continued)

(58) Field of Classification Search
CPC .... A61B 2034/2048; A61B 2090/3764; A61B 6/547; A61B 6/463; G06T 7/70
See application file for complete search history.

(56) References Cited

U.S. PATENT DOCUMENTS 6,069,932 A 5/2000 Peshkin et al.
6,285,902 B1 9/2001 Kienzle, III et al.
(Continued)

FOREIGN PATENT DOCUMENTS

WO 2012152264 A1 11/2012
WO 2015022067 A1 2/2015
(Continued)

OTHER PUBLICATIONS

English language abstract and machine-assisted English translation for WO 2012/152264 A1 extracted from espacenet.com database dated Dec. 1, 2022, 14 pages.
(Continued)

*Primary Examiner* — Carolyn A Pehlke
(74) *Attorney, Agent, or Firm* — Howard & Howard Attorneys PLLC

(57) ABSTRACT

The present teachings generally provide for a surgical navigation system for use with an x-ray imaging device. The x-ray imaging device acquires x-ray images of an anatomical structure of interest at an angular position. The surgical navigation system includes a localizer with a tracking sensor, a gravity vector sensor coupled to the tracking sensor, a tracking device configured to be coupled to the C-arm so as to be movable with the C-arm between a plurality of angular positions. The tracking device comprises a tracking element detectable by the tracking sensor. A computer processor is operatively coupled with the localizer and configured to implement an imaging routine that receives tracking data from the tracking sensor and a gravity vector from the gravity vector sensor, generating an image vector indicative of the angular position at which the x-ray image was acquired.

11 Claims, 6 Drawing Sheets

(51) Int. Cl.
*G06T 7/70* (2017.01)
*A61B 34/00* (2016.01)
*A61B 6/02* (2006.01)
*A61B 90/00* (2016.01)

(52) U.S. Cl.
CPC ............... *A61B 34/25* (2016.02); *G06T 7/70* (2017.01); *A61B 6/022* (2013.01); *A61B 2034/2055* (2016.02); *A61B 2034/2057* (2016.02); *A61B 2034/256* (2016.02); *A61B 2090/3764* (2016.02)

(56) References Cited

U.S. PATENT DOCUMENTS

| | | | |
|---|---|---|---|
| 6,477,400 B1 | 11/2002 | Barrick | |
| 6,739,752 B2 | 5/2004 | Sabczynski et al. | |
| 6,770,028 B1 | 8/2004 | Ali et al. | |
| 6,771,734 B2 | 8/2004 | Hebecker et al. | |
| 7,065,393 B2 | 6/2006 | Sati et al. | |
| 7,088,798 B2 | 8/2006 | Chen et al. | |
| 7,277,594 B2 | 10/2007 | Hofstetter et al. | |
| 7,303,470 B2 | 12/2007 | George et al. | |
| 7,303,475 B2 | 12/2007 | Britt et al. | |
| 7,570,791 B2 | 8/2009 | Frank et al. | |
| 7,883,410 B2 | 2/2011 | Soukup et al. | |
| 7,998,067 B2 | 8/2011 | Kimoto et al. | |
| 8,022,990 B2 | 9/2011 | Li et al. | |
| 8,036,730 B1 | 10/2011 | Damadian et al. | |
| 8,429,229 B2 | 4/2013 | Sepich et al. | |
| 8,467,851 B2 | 6/2013 | Mire et al. | |
| 8,545,322 B2 | 10/2013 | George et al. | |
| 8,675,939 B2 | 3/2014 | Moctezuma de la Barrera | |
| 8,727,854 B2 | 5/2014 | George et al. | |
| 8,848,860 B2 | 9/2014 | Yazaki | |
| 8,933,935 B2 | 1/2015 | Yang et al. | |
| 8,956,219 B2 | 2/2015 | Soukup et al. | |
| 9,008,279 B2 | 4/2015 | Grzeda et al. | |
| 9,033,788 B2 | 5/2015 | George et al. | |
| 9,117,008 B2 | 8/2015 | Iizuka et al. | |
| 9,248,000 B2 | 2/2016 | Sarvestani et al. | |
| 9,286,762 B2 | 3/2016 | George et al. | |
| 9,367,985 B2 | 6/2016 | Dempsey et al. | |
| 9,452,351 B2 | 9/2016 | George et al. | |
| 9,452,359 B2 | 9/2016 | Sepich et al. | |
| 9,523,706 B2 | 12/2016 | Hatlestad et al. | |
| 9,554,731 B2 | 1/2017 | Malchau et al. | |
| 9,566,120 B2 | 2/2017 | Malackowski et al. | |
| 9,572,548 B2 | 2/2017 | Moctezuma de la Barrera | |
| 9,579,043 B2 | 2/2017 | Chien et al. | |
| 9,867,588 B2 | 1/2018 | Amiri | |
| 9,968,502 B2 | 5/2018 | Hight et al. | |
| 10,172,585 B2 | 1/2019 | Amiri | |
| 10,743,944 B2 | 8/2020 | Frasier et al. | |
| 10,799,299 B2 | 10/2020 | Lee et al. | |
| 10,806,415 B2 | 10/2020 | Bailey et al. | |
| 10,828,001 B2 | 11/2020 | Yoshida | |
| 10,874,371 B2 | 12/2020 | Gorges et al. | |
| 10,881,363 B2 | 1/2021 | Jans et al. | |
| 11,000,252 B2 | 5/2021 | Van Geoff | |
| 11,089,975 B2 | 8/2021 | Frasier et al. | |
| 11,100,668 B2 | 8/2021 | Crawford et al. | |
| 11,253,216 B2 | 2/2022 | Crawford et al. | |
| 11,317,973 B2 | 5/2022 | Calloway et al. | |
| 2003/0004438 A1 | 1/2003 | Berthonnaud et al. | |
| 2004/0015077 A1 | 1/2004 | Sati et al. | |
| 2010/0312103 A1* | 12/2010 | Gorek | A61B 34/20 600/425 |
| 2011/0164721 A1 | 7/2011 | Jank et al. | |
| 2012/0253200 A1* | 10/2012 | Stolka | A61B 90/13 600/459 |
| 2019/0231283 A1 | 8/2019 | Jans et al. | |
| 2020/0029937 A1 | 1/2020 | Osumi et al. | |
| 2020/0237336 A1* | 7/2020 | Marino | A61B 6/547 |
| 2020/0253383 A1 | 8/2020 | Young et al. | |
| 2021/0042917 A1 | 2/2021 | Hirai et al. | |
| 2021/0169577 A1 | 6/2021 | Hornecker et al. | |
| 2021/0186617 A1 | 6/2021 | Gorek et al. | |
| 2022/0079685 A1 | 3/2022 | Shimamoto et al. | |
| 2022/0113810 A1 | 4/2022 | Isaacs et al. | |
| 2022/0175461 A1 | 6/2022 | Hananel et al. | |
| 2022/0303435 A1 | 9/2022 | Ramirez Luna et al. | |

FOREIGN PATENT DOCUMENTS

| | | |
|---|---|---|
| WO | 2016181447 A1 | 11/2016 |
| WO | 2019072916 A1 | 4/2019 |

OTHER PUBLICATIONS

English language abstract and machine-assisted English translation for WO 2015/022067 A1 extracted from espacenet.com database dated Nov. 17, 2022, 14 pages.

English language abstract and machine-assisted English translation for WO 2016/181447 A1 extracted from espacenet.com database dated Nov. 17, 2022, 9 pages.

English language abstract and machine-assisted English translation for WO 2019/072916 A1 extracted from espacenet.com database dated Nov. 17, 2022, 22 pages.

* cited by examiner

GRAVITY BASED PATIENT IMAGE ORIENTATION DETECTION

BACKGROUND

Navigation systems for tracking the position of one or more work targets located inside a body, either alone or in relation to one or more various working instruments, are used in many types of applications. One application in which navigation systems are commonly used is in the field of navigated surgical procedures. In this field, surgical navigation systems are now commonly used to assist in planning a surgical procedure or executing a planned surgical procedure, so as to improve the accuracy of the surgical procedure and minimize the invasiveness thereof.

It is common for surgical navigation systems to use X-ray imaging systems. The X-ray imaging systems typically uses a C-arm configuration. The C-arm includes a C-shaped recording unit on an adjustable and moveable mounting structure opposite an x-ray source. Typically, the x-ray source is mounted on one end of the C-arm, and the imaging portion is mounted opposite of the x-ray source on the other end of the C-arm. The C-arm is positioned around an object to be imaged, such as an anatomical feature of a patient, and an image is taken in a first position. The C-arm may then be moved into another position to acquire another image of the same anatomical feature from a different viewpoint. Of particular interest in surgical procedures are lateral and anterior-posterior (A-P) views. Known systems require a surgeon or other member of the surgery team to manually correlate the lateral and A-P views, for example, on a user interface for the system to properly utilize the images. For example, the first image is taken in a first position or view (e.g., a lateral view) and when a second or subsequent image is taken in a second position or view (e.g., anterior-posterior view), a surgery team member would have to manually switch the display to show the newly acquired second/subsequent image from the first image.

Typically, x-ray images are taken for visual navigation systems in a lateral pose and an anterior-posterior pose for locating the anatomical feature and for developing a pair of 2D representative images which then have surgical instrument representations overlaid for intra-operative tracking. Visual navigation systems use imagine based navigation from preoperative and intraoperative images along with some form of patient tracker. Visual navigation is used primarily with cranial, spine, and ENT procedures. The images can be aligned with a model in the navigation system to provide intraoperative positions of the anatomical features of interest.

Although fluoroscopy is common in surgical navigation systems for pre-operative, and intraoperative applications, it would be attractive to have a surgical navigation system which automatically recognized the position the C-arm is in when an image is take, increasing workflow efficiency.

SUMMARY

The present teachings generally provide for a surgical navigation system for use with an x-ray imaging device. The x-ray imaging device may be configured to acquire x-ray images of an anatomical structure of interest at one of a plurality of angular positions relative to a direction toward center of Earth gravity. The surgical navigation system may comprise a localizer with a tracking sensor, and a gravity vector sensor coupled to the tracking sensor. The gravity vector sensor may be configured to detect the direction toward center of Earth gravity regardless of an orientation of the tracking sensor. The surgical navigation system may further include a tracking device configured to be coupled to the C-arm imaging device so as to be movable with movement of the C-arm imaging device between the plurality of angular positions. The tracking device may comprise a tracking element detectable by the tracking sensor. The surgical navigation system may include a computer processor operatively coupled to the localizer. The computer processor may be configured to implement an imaging routine. The imaging routine may operate by receiving tracking data from the tracking sensor and a gravity vector from the gravity vector sensor, to generate an image vector based on the tracking data with the image vector being indicative of the one of the plurality of angular positions at which the x-ray image was acquired. The computer processor may then determine an angle between the image vector and the gravity vector and assigning an image identifier to the x-ray image based on the determined angle. The image identifier may be configured to provide an indication of the one of the plurality of angular position at which the x-ray image was acquired. A display may be coupled to the computer processor such that the display is configured to display the x-ray image with the image identifier corresponding to one of the plurality of angular positions at which the x-ray image was acquired. The computer processor may be configured to display a visual representation of a surgical instrument onto the x-ray image on the display. The visual representation may appear from one of at least two different perspectives based on the image identifier.

The surgical navigation system may further include a memory coupled to the computer processor. The computer processor may be configured to store a first predefined range of angles and a second predefined range of angles exclusive from the first predefined range of angles. The implementation of the imaging routine by the computer processor may further comprise receiving the first and second predefined ranges of angles from the memory, determining whether the determined angle is within the first predefined range of angles or the second predefined range of angles, and assigning the image identifier to the x-ray image when the determined angle is within the first predefined range of angles and not within the second predefined range of angles. The first predefined range of angles may be greater than 45° to less than or equal to 135°, and the second predefined range of angles may be greater than 0° to less than or equal to 45°, and greater than 135° to less than or equal to 180°. The image identifier may be a lateral image identifier or an anterior-posterior image identifier configured to be displayed along with the x-ray image to provide the indication that the x-ray image is a lateral x-ray image of the anatomical structure. The memory may be configured to store a plurality of predefined ranges of angles exclusive from one another. The image identifier may be a plurality of image identifiers. Each of the plurality of image identifiers corresponding to one or more of the plurality of predefined ranges of angles. The imaging routine may comprise retrieving the predefined ranges of angles from the memory, determining which one of the predefined ranges of angles the determined angle is within, and assign one of the plurality of image identifiers to the x-ray image based on the determined one predefined range of angles. The imaging routine may further comprise updating the x-ray image on the display with a second x-ray image on the display when the second x-ray image is assigned a second image identifier the same as the first image identifier. The second image identifier may be based on a second determined angle between a second image vector being indicative of one of the plurality of angular positions at which the second x-ray image was acquired, and the gravity vector.

The teachings further provide for a method for acquiring an x-ray image of an anatomical structure with a C-arm imaging device and identifying the x-ray image on a display. A navigation system may be provided including a tracking device coupled to the C-arm imaging device and including a tracking element detectable by a tracking sensor of a localizer, a gravity vector sensor configured to detect the direction toward center of Earth gravity regardless of an orientation of the tracking sensor, and a computer processor. The method may comprise acquiring a first of the x-ray images with the C-arm imaging device at a first angular position. The tracking sensor may detect a first pose of the tracking device as the first x-ray image is acquired. The computer processor may generate a first image vector based on the first pose of the tracking device and a gravity vector based on the gravity vector sensor. The computer processor may determine a first angle between the first image vector and the gravity vector. The computer processor may assign a first image identifier to the first x-ray image based on the first determined angle and displaying the first x-ray image on the display. The C-arm imaging device may acquire a second of the x-ray images at a second angular position different than the first angular position. The tracking sensor may detect a second pose of the tracking device as the second x-ray image is acquired. The computer processor may generate a second image vector based on the second pose of the tracking device. The computer processor may determine a second angle between the second image vector and the gravity vector and assign a second image identifier to the second x-ray image based on the second determined angle. The second x-ray image may be displayed on the display. The step of displaying the first x-ray image on the display may be performed after the step of assigning the first image identifier and prior to the step of acquiring the second x-ray image. The first image identifier may correspond with the first x-ray image being one of an anterior-posterior (A-P) x-ray image and a lateral x-ray image of the anatomical structure. The second image identifier corresponds with the second x-ray image being one of another A-P x-ray image and another lateral x-ray image of the anatomical structure.

The navigation system may include a memory configured to store a first predefined range of angles and a second predefined range of angles exclusive from the first predefined range of angles. The computer processor may then determine whether the first determined angle is within the first predefined range of angles and assign the first image identifier to the first x-ray image when the first determined angle is within the first predefined range of angles. Alternatively, the computer processor may determine whether the second determined angle is within the second predefined range of angles and assign the second image identifier to the second x-ray image when the second determined angle is within the second predefined range of angles. The first predefined range of angles may be greater than 45° to less than or equal to 135°, and the second predefined range of angles may be greater than 0° to less than or equal to 45°, and greater than 135° to less than or equal to 180°.

The tracking element of the tracking device may be a first tracking element and a second tracking element may be located on a surgical instrument. A pose of the surgical instrument may be tracked by detecting the second tracking element with the tracking sensor. The pose of the surgical instrument may be displayed by overlaying a visual representation of the surgical instrument onto at least one of the first and second x-ray images on the display with the visual representation appearing from one of at least two different perspectives based on the first and second image identifiers. The first and second image identifiers are displayed on the display and respectively associated with the first and second x-ray images.

The present teachings further include a method for acquiring x-ray images of an anatomical structure with a C-arm imaging device. A navigation system may be provided and include a tracking device coupled to the C-arm imaging device which is detectable by a tracking sensor of a localizer, a gravity vector sensor configured to detect the direction toward center of Earth gravity regardless of an orientation of the tracking sensor, and a computer processor. A first of the x-ray images with the C-arm imaging device may be acquired at an angular position. The tracking sensor may detect a pose of the tracking device as the first x-ray image is acquired. The computer processor may be used to generate a first image vector based on the pose of the tracking device. The computer processor may receive a gravity vector from the gravity vector sensor. The computer processor may determine an angle between the first image vector and the gravity vector. The gravity sensor may be coupled to the localizer. The computer processor may determine a first image identifier for the first x-ray image based on the determined angle and display the first x-ray image on the display in a manner based on the image identifier. A second of the x-ray images may be acquired with the C-arm imaging device. The computer processor may generate a second image vector based on the pose of the tracking device and determine an angle between the second image vector and the gravity vector. The computer processor may determine a first image identifier for the first x-ray image based on the determined angle and update the first x-ray image on the display with the second x-ray image if the second image identifier is the same as the first image identifier. The computer processor may determine that the first image identifier and/or the second image identifier further identifies the x-ray image as either a lateral x-ray image or an anterior-posterior (A-P) x-ray image. The x-ray image may be identified as the A-P x-ray image if the determined angle is within a first predefined range of angles or as the lateral x-ray image if the determined angle is within a second predefined range of angles exclusive from the first predefined range of angles. The first predefined range of angles may be greater than 45° to less than or equal to 135°, and the second predefined range of angles may be greater than 0° to less than or equal to 45°, and greater than 135° to less than or equal to 180°. A visual representation of a surgical instrument may be overlaid onto the x-ray image on the display with the visual representation appearing from one of at least two different perspectives based on whether the x-ray image is identified as the lateral x-ray image or the A-P x-ray image.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

Figure 1:
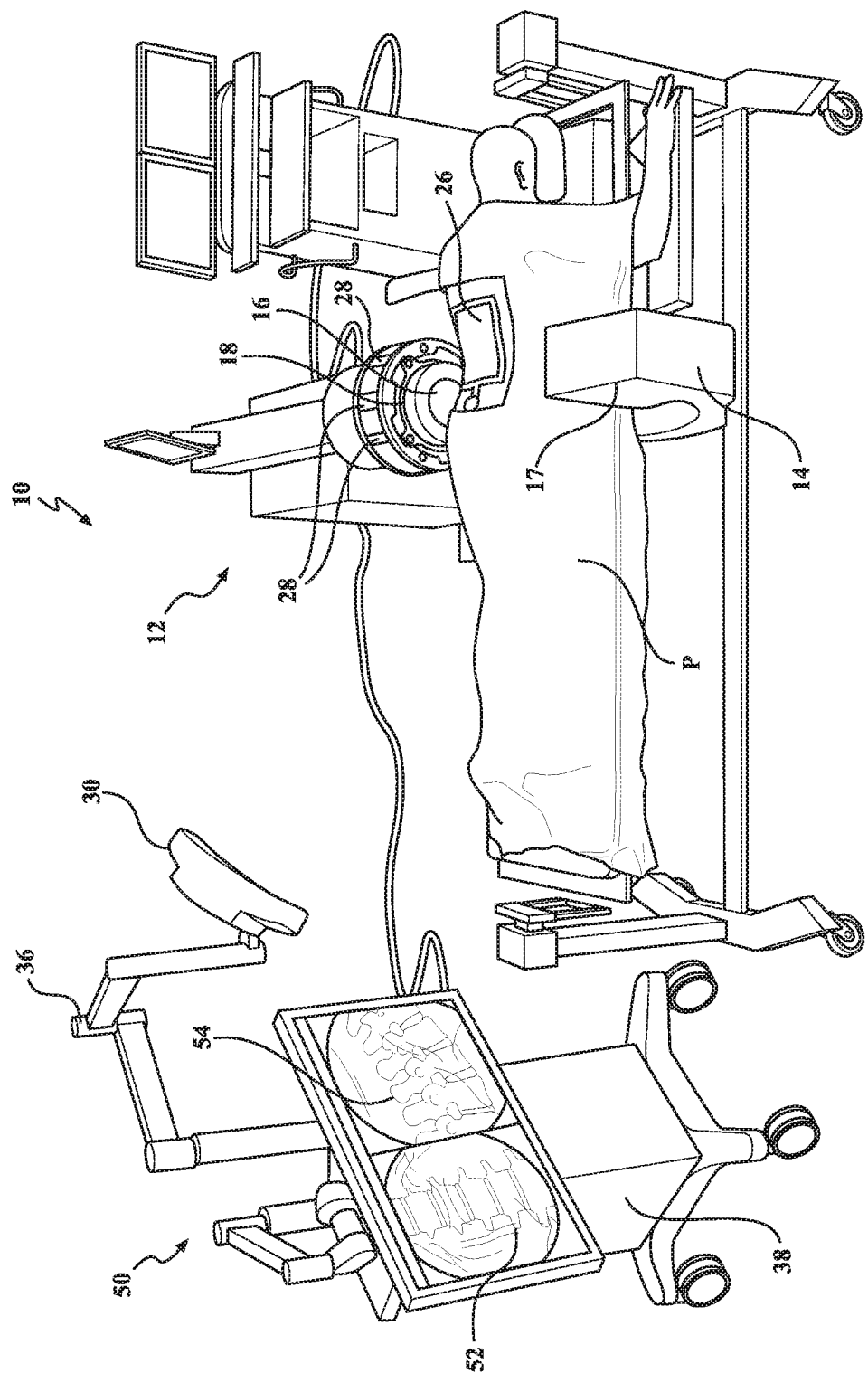
FIG. 1 illustrates a perspective view of the surgical navigation system.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the present disclosure is not intended to be exhaustive or limiting. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings generally relate to a surgical navigation system for use in surgery. Particularly, the surgical navigation system may be used for pre-operative planning, intraoperative use, or post-operative follow up. The surgical navigation system may function with an x-ray imaging device to acquire x-ray images of one or more anatomical objects of interest and display the x-ray images to a surgeon or surgery team. For example, the surgical navigation system may take and display an x-ray image of a particular anatomical feature or region (e.g. knee, spine, ankle, foot, neck, hip, arm, leg, rib cage, hand, shoulder, head, the like, or a combination thereof). The surgical navigation system may function to superimpose an image of surgical instruments over the displayed x-ray image of the anatomical feature, displaying the surgical instruments relative the anatomical feature. For example, the surgical navigation system may superimpose the image of a surgical instrument relative to imaged anatomical feature so that the surgeon may observe the relative distance of the surgical instrument and the target portion of the anatomical feature which is to be affected by the surgical instrument. The surgical navigation system may function to acquire multiple x-ray images. For example, a first x-ray image may be acquired in a first pose, and the surgical navigation system displays that image at a first orientation corresponding to the position of the C-arm. A second x-ray image may then be taken after the first x-ray image. The surgical system may then determine whether the image is in the first pose or a second pose based on information generated by the tracking sensors and a gravity vector sensor. The surgical navigation system may automatically correlate the second image with its correct orientation. The surgical navigation system may replace the first image if the image pose is the same, and/or display the second image in a second pose different than the first pose. The surgical navigation system may automatically update the displayed images as additional images are acquired at the same positions. The surgical navigation system may comprise a computer processor connected with an x-ray imaging device, a localizer, and the gravity vector sensor. The localizer may monitor the position of an image tracking device located on the imaging portion of the x-ray imaging device. The surgical navigation system may be connected with a display configured to present one or more images acquired by the x-ray imaging device.

The surgical navigation system may be connected with an x-ray imaging device. The x-ray imaging device may function to acquire images of the patient or anatomical features of the patient's body. The x-ray imaging device may include a structure with an x-ray emitting portion (e.g., x-ray tube) and an imaging portion (e.g., x-ray detector). The x-ray imaging device may be configured as a C-arm. The C-arm may include the x-ray tube at a first end of the C-arm and the x-ray detector located on the opposing second end of the C-arm. The x-ray tube and the x-ray detector may be at a fixed distance from each other. An imaging region may be defined in the center of the c-shape, between the x-ray tube and the x-ray imaging portion. A patient or a portion of a patient may be located in the center section of the C-arm, between the x-ray tube and the x-ray detector, so that a specific portion of the patient may be imaged. The C-arm may be moved between a plurality of positions. The C-arm may be rotated about a patient or anatomical feature of interest, tilted relative to a patient or particular anatomical feature, raised, lowered, repositioned, or a combination thereof. During movement, the imaging portion and the x-ray source maintain a fixed relationship, keeping the same distance on the opposite ends of the C-arm.

An image tracking device may be removably coupled with the imaging portion of the C-arm. The image tracking device may function to indicate the position or pose of the imaging portion of the x-ray imaging device. The image tracking device may be disposed over the imaging portion while allowing the imaging portion to acquire the desired x-ray images of the patient or object of interest. The image tracking device may include one or more tracking elements which may be used in conjunction with a localizer. The one or more tracking elements may be sensed by the localizer so that the localizer can track the position of the one or more tracking elements, conveying the position of the image tracking device to the localizer.

The surgical navigation system may include a plurality of tracking elements. The tracking elements may function to be sensed and tracked by the localizer. The image tracking device, the one or more surgical instruments, the one or more patient trackers, or a combination thereof may each include at least one of tracking elements. The tracking elements may be any feature or structure adapted to be sensed by the surgical navigation system with the localizer. In some arrangements, the tracking elements may include an LED, a reflective surface, a reflective pattern, a magnetic coil, a radio transmitter, and/or an optically identifiable geometric shape that uniquely defines position and orientation perceivable by the localizer.

The surgical navigation system may include the localizer. The localizer may function to monitor and track the image tracking device on the imagining portion of the C-arm, surgical instruments, patient trackers, or a combination thereof. One suitable localizer is the FP6000 tracking camera manufactured by Stryker Corporation (Kalamazoo, Mich.). The localizer may function to send information regarding the position of the tracking device, surgical instruments, patient tracker, or a combination thereof to a computer processor. The localizer may include one or more of the tracking sensors, the gravity vector sensor, or both. The localizer may use an optical means, a magnetic means, a radio frequency means, or a combination thereof for monitoring the location of the imagine tracking device, the surgical instruments, the patient tracker, or a combination thereof. The optical means of detection may function in the visible light spectrum, the infrared spectrum, or both. The magnetic means of detection may acknowledge and track differences in magnetic fields. The radio frequency means of detection may function to track radio frequencies. The localizer may be in a fixed position or a moveable position. For example, the localizer may be attached to a stationary stand and positioned in the surgery room. In another example, the localizer may be located on a moveable base. The localizer may be placed in any location within the operation room which has a line of sight to the tracking elements on the image tracking device, the surgical instruments, the patient tracker, or a combination thereof.

The localizer may include one or more tracking sensors. The tracking sensors may function to identify the position of the image tracking device on the imaging portion of the C-arm. The tracking sensors may function to acquire positional information of the image tracking device, the surgical instruments, the patient trackers, or a combination thereof, communicating the corresponding positional information to the computer processor. The tracking sensors may have an optical means, a magnetic means, a radio frequency means, or a combination thereof to sense the position of the image tracking device, the surgical instruments, the patient tracker, or a combination thereof at the moment an x-ray image is acquired. The optical means may function in the visible light spectrum, the infrared spectrum, or both. For example, the one or more tracking sensors may be one or more cameras, such as CCD, CMOS, optical image, or a combination thereof. The magnetic means of detection may acknowledge and track differences in magnetic fields. The radio frequency means may function to track radio frequencies. The tracking sensor may be positioned in any location which has a line of sight to the tracking elements on the image tracking device, the surgical instruments, the patient tracker, or a combination thereof.

The surgical navigation system may track the position and movement of one or more surgical instruments. The one or more surgical instruments may function to probe, cut, saw, drill, grind, debride, cauterize, probe, the like, or a combination thereof. The surgical instruments may be handheld, robotic, powered, nonpowered, or a combination thereof. The surgical instruments may include at least one tracking element. The tracking element may be registered with the localizer so that the localizer may track the position of the surgical instruments in real time. The surgical instruments may be tracked and displayed in real time over the images acquired by the x-ray imaging device so that the location of the working end of the surgical instruments relative the anatomical feature is known.

The surgical navigation system may include one or more patient trackers on a patient. The patient tracker may function with the navigation system to detect and compensate for movement and deformations during a procedure, adjusting so that the surgeon and/or surgery team have a real-time location of the surgical instruments, the target anatomical feature, or both. The patient tracker may include at least one tracking element. The patient tracker may be any shape that is suitable to track movement and compression of a patient during a procedure. The patient tracker is not limited to a particular shape or form, and may be rigid, flexible, and/or have multiple separate sections. In one example, the patient tracker has a plurality of tracking elements, such as LEDs, disposed on a flexible substrate having the shape of a generally rectangular frame with an open window there through that can be removably secured to the patient's skin with adhesive.

The surgical navigation system may include a gravity vector sensor. The gravity vector sensor may function to detect the direction toward center of Earth gravity, regardless of position or orientation. The direction toward the center of Earth gravity is a gravity vector. The gravity vector sensor determines the gravity vector regardless of the position of the gravity vector sensor. The gravity vector may be used as a reference point to determine the position of another object, since the gravity vector sensor provides the gravity vector which is always toward the center of Earth gravity. For example, the gravity vector may be referenced to determine the angular position of the image tracking device by comparing the relative position of the image tracking device to the gravity vector. The gravity vector sensor may be located anywhere as long as a connection with the computer processor is maintained. For example, the gravity vector sensor may be located within the localizer. The gravity vector sensor may be connected with the computer processor through a wired connection, a wireless connection, a network, or a combination thereof.

The surgical navigation system may include a computer processor. The computer processor may function to analyze the information received from the localizer and the gravity vector sensor. The computer processor may function to determine the pose of one or more images acquired by the x-ray imaging device. The computer processor may function to process the positional data collected by the localizer with the images acquired by the x-ray imaging device so that the x-ray images are displayed based on the sensed position of the image tracking device relative to the gravity vector. The computer processor may receive data from the tracking sensor and the gravity vector sensor. The computer processor may calculate an image vector of the image tracking device received from the tracking sensor within the localizer. The image vector is the angular position of the image tracking device on the C-arm of the x-ray imaging device. The computer processor may calculate the sensed position of the image tracking device at the moment an image is taken by the x-ray imaging device by generating the image vector based on the tracking sensors and tracking elements of the image tracking device, and the gravity vector from the gravity vector sensor. The computer processor then calculating a determined angle which is the angular difference between the perceived location of the image tracking device and the gravity vector. The computer processor may analyze the determined angle in a database or a library, and assign an image orientation based on the sensed data from the moment the image was acquired by the x-ray imaging device. The computer processor may then send the image capture data to the image display to be displayed to the surgeon and/or surgery team in the appropriate orientation automatically. The computer processor analyzes and determines the angular position and orientation of each image the x-ray imaging device acquires. The computer processor may automatically update a displayed image with a subsequently acquired image when the determined angle of that image falls within the same predefined range angles. The computer processor may further process positional data of the surgical instruments, the patient trackers or both. For example, the computer processor may display the position of the surgical instrument(s) onto a displayed first perspective image, a displayed second perspective image, or both simultaneously, showing the position of the one or more surgical instruments relative the anatomical feature as the surgical instrument is moved during the procedure.

The computer processor may include a memory. The memory may function to hold one or more libraries, databases, lookup tables, or a combination thereof. The memory may function to store data relating to the position of the C-arm (image vector), the images taken by the x-ray imaging device, the gravity vector value, a first predefined range of angels, a second predefined range of angles exclusive from the first predefined range of angles, a plurality of image identifiers corresponding to the position of the image tracking device, or a combination thereof. The memory may be transitory memory, non-transitory memory, or both. In one example, the memory includes a first predefined range and a second predefined range exclusive of the first predefined range, and the computer processor compares the determined angle of the acquired x-ray image with the first predefined range of angles and the second predefined range of angles to determine which predefined range the determined angle falls within. Once calculated, the computer processor assigns an image identifier to the x-ray image and shows the x-ray image on the display in the correct orientation. The memory may include multiple predefined ranges, each predefined range being exclusive from each other. Each of the predefined ranges is associated with an image identifier.

The computer processor may assign an image identifier based on the predefined range which the determined angle falls within. Each of the image identifiers may function to provide an indication of the one of the plurality of angular position at which the x-ray image was acquired. The computer processor may designate a unique image identifier for each of the plurality of predefined ranges of angles. For example, a first predefined range of angles may be greater than 45° to less than or equal to 135° and correspond with an anterior-posterior (A-P) image identifier. In another example, the second predefined range of angles may be greater than 0° to less than or equal to 45°, and greater than 135° to less than or equal to 180° and correspond with a lateral image identifier. The image identifier corresponding to the angular position of the x-ray image may be presented on the display with the x-ray image.

Turning to FIG. 1, a perspective view of the surgical navigation system 10 and the x-ray imaging device 12 are illustrated. The x-ray imaging device 12 including a C-arm 14 with an imaging portion 16 and x-ray tube 17. Connected with the imaging portion 16 is the tracking device 18. The tracking device 18 is disposed over the imaging portion 16 of the x-ray imaging device 12 to transmit data relating to the position of the imaging portion 16. The C-arm 14 is shown surrounding a patient P such that the imagining portion 16 and the x-ray tube 17 are perpendicular to the spine of the patient P.

The localizer 30 is connected with moveable arm 36, attaching the localizer 30 to the computer processor 38 configured as a moveable unit. The localizer 30 may be placed in any position within the vicinity of the surgical procedure and x-ray imaging device 12 to accommodate spacing issues within the surgical area. The localizer 30 is configured to track the tracking elements 28 of the image tracking device 18 on the imaging portion 16 of the C-arm 14. The localizer 30 tracks the movement of the image tracking device 18 between positions by sensing the position of the tracking elements 28. As the imaging portion 16 is moved between a plurality of positions (See FIGS. 4A and 4B), the localizer 30 collects location data, sending the location data of the image tracking device 18, as well as the gravity vector data from the gravity vector sensor 32, to the computer processor 38. The localizer 30 may be further configured to track a patient tracker 26, for example, the SpineMask Tracker manufactured by Stryker Leibinger GmbH & Co. KG (Freiberg, Germany).

Figure 2:
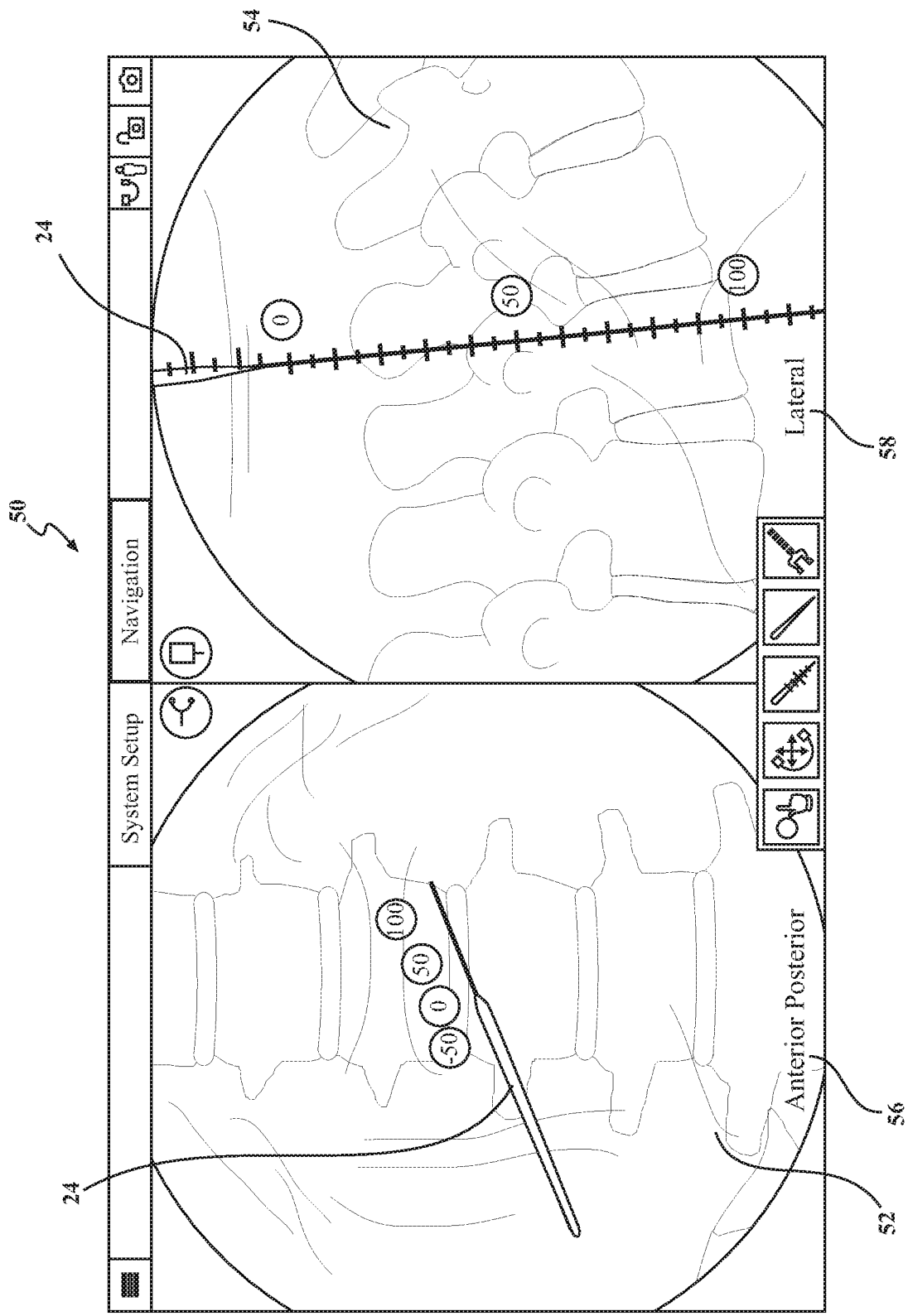
FIG. 2 illustrates a display showing an anterior-posterior view and a lateral view along with a surgical instrument and its location relative a target bone area.

The localizer 30 and display 50 are shown as being located on the computer processor 38. In one implementation, the display 50 and localizer 30 may be separate structures from the computer processor 38. The display 50 is shown as having two screens, each screen displaying an image. FIG. 2 is a closeup of display 50 with the first image 52 in an anterior-posterior view of the anatomical feature and the surgical tool 24, and the second image 54 is in a lateral view of the of the surgical tool 24 and the anatomical feature, which, in this example, is a portion of the spine of patient P. The first image 52 is displayed with a first image identifier 56 indicating "anterior-posterior" and the second image 54 shown with the second image identifier 58 indicating "lateral." In the first displayed image 52, the surgical tool 24 is shown at a plane contacting the spine from the A-P view. The second displayed image 54 shows the surgical tool 24 contacting the spine from the lateral view. By providing both the A-P view and the lateral view, the surgeon can ascertain the position of the surgical tool 24 relative to the anatomical feature. It is contemplated that the image identifier may not be displayed on the display 50, but rather exist as data assigned to the images, which may be utilized by the computer processor 38 for subsequent aspects of the image routine.

Figure 3:
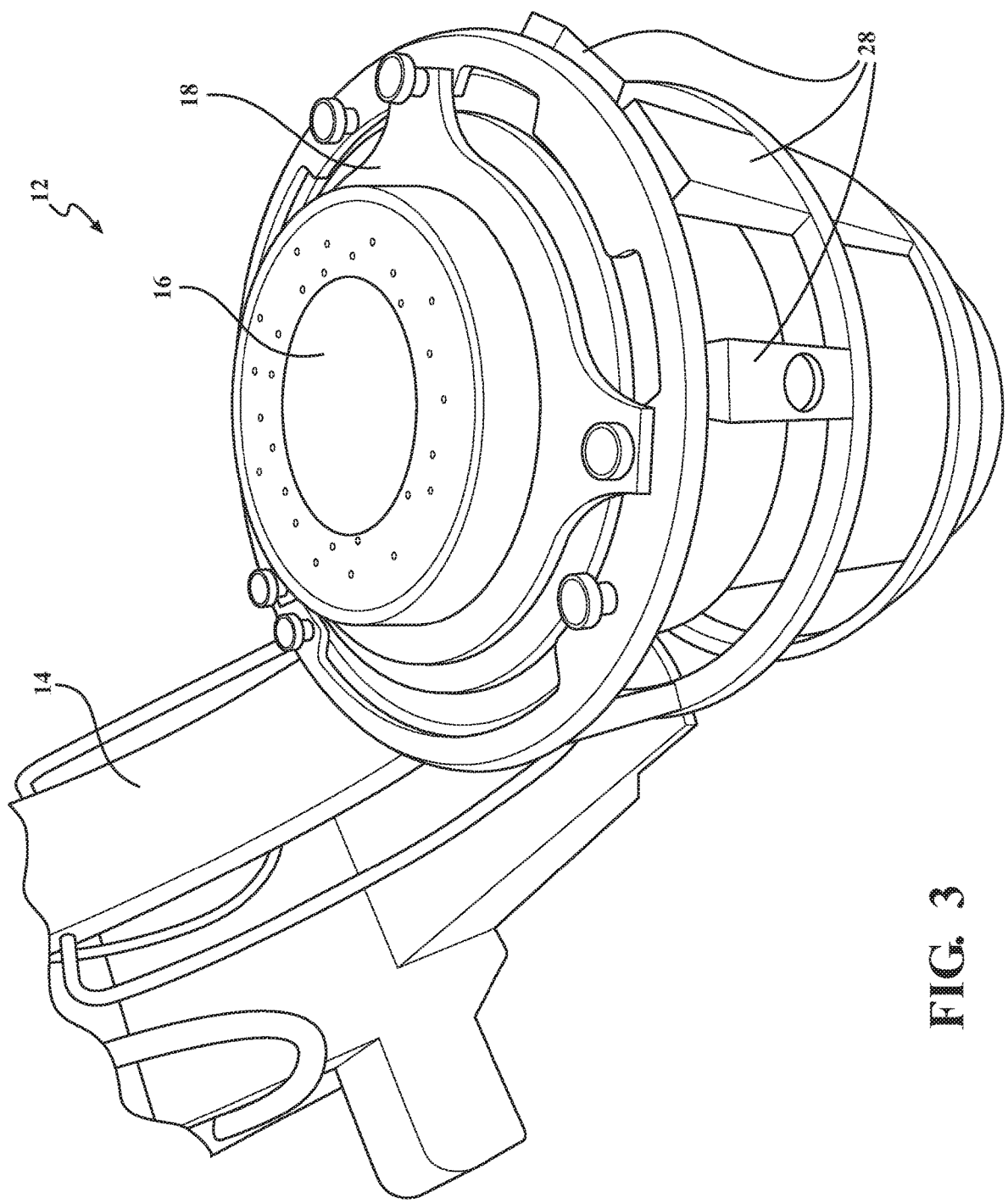
FIG. 3 shows an x-ray imaging device including a C-arm and a moveable imaging portion, the imaging portion coupled with a tracking device.

FIG. 3 is a perspective view of the image tracking device 18 disposed over the imaging portion 16 of the C-arm. The image tracking device 18 includes tracking elements 28 which are configured to be tracked by the localizer 30. The localizer 30 as pictured in FIG. 1, optically tracks the tracking elements 28 of the image tracking device 18 as the imaging portion 16 of the C-arm 14 is moved from position to position. When the imaging portion 16 of the C-arm 14 is moved from position to position and taking x-ray images, the localizer 30 determines the coordinates of the pose of the tracking device 18 at the moment each of the x-ray images are acquired. The localizer 30 sends the coordinates of the pose to the computer processor 38 to be analyzed with the gravity vector 42.

Figure 4A:
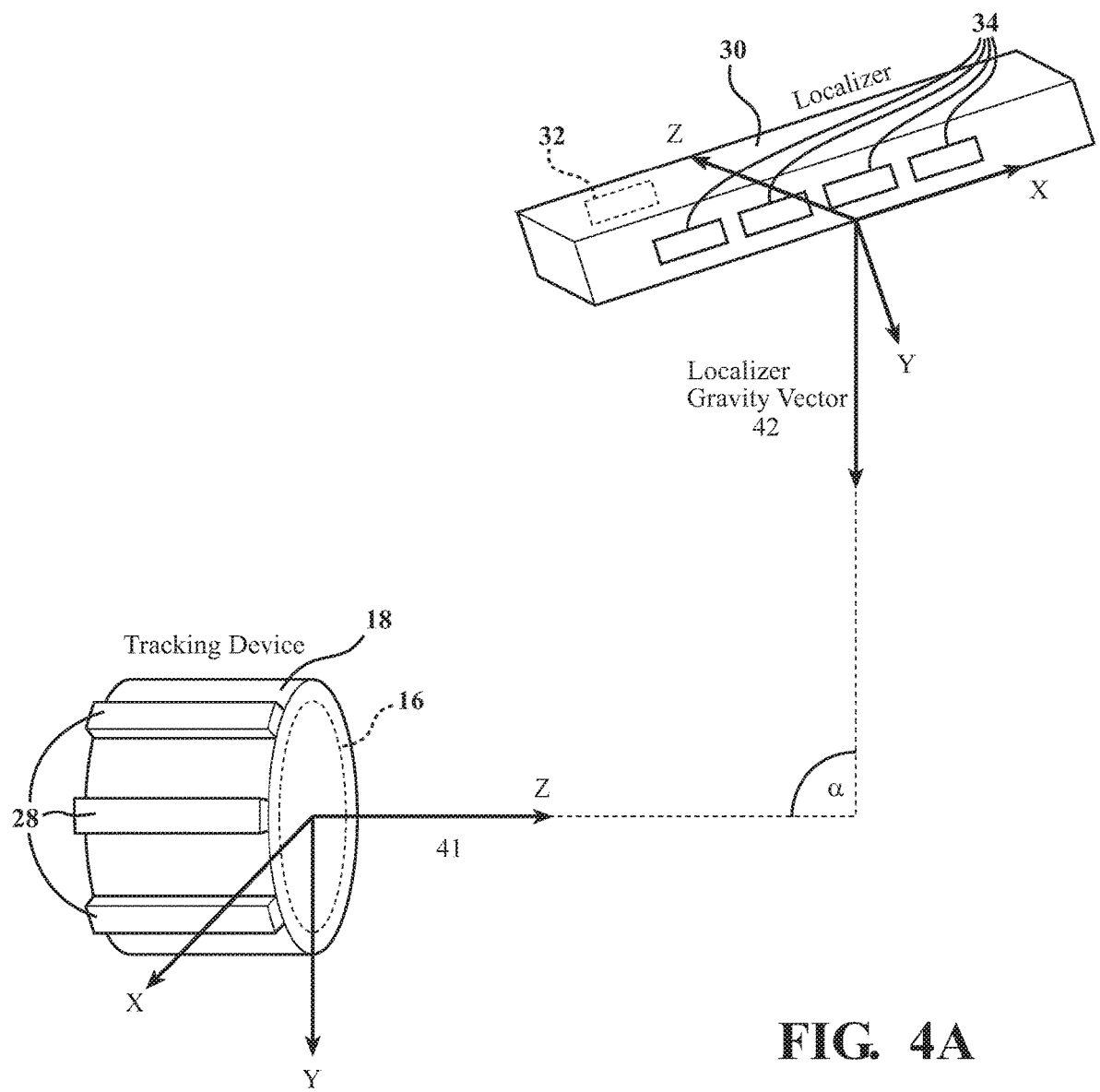
FIG. 4A illustrates the tracking device and localizer with the optical tracking sensor and gravity vector sensor, and the associated angle vectors in a first representative position.
Figure 4B:
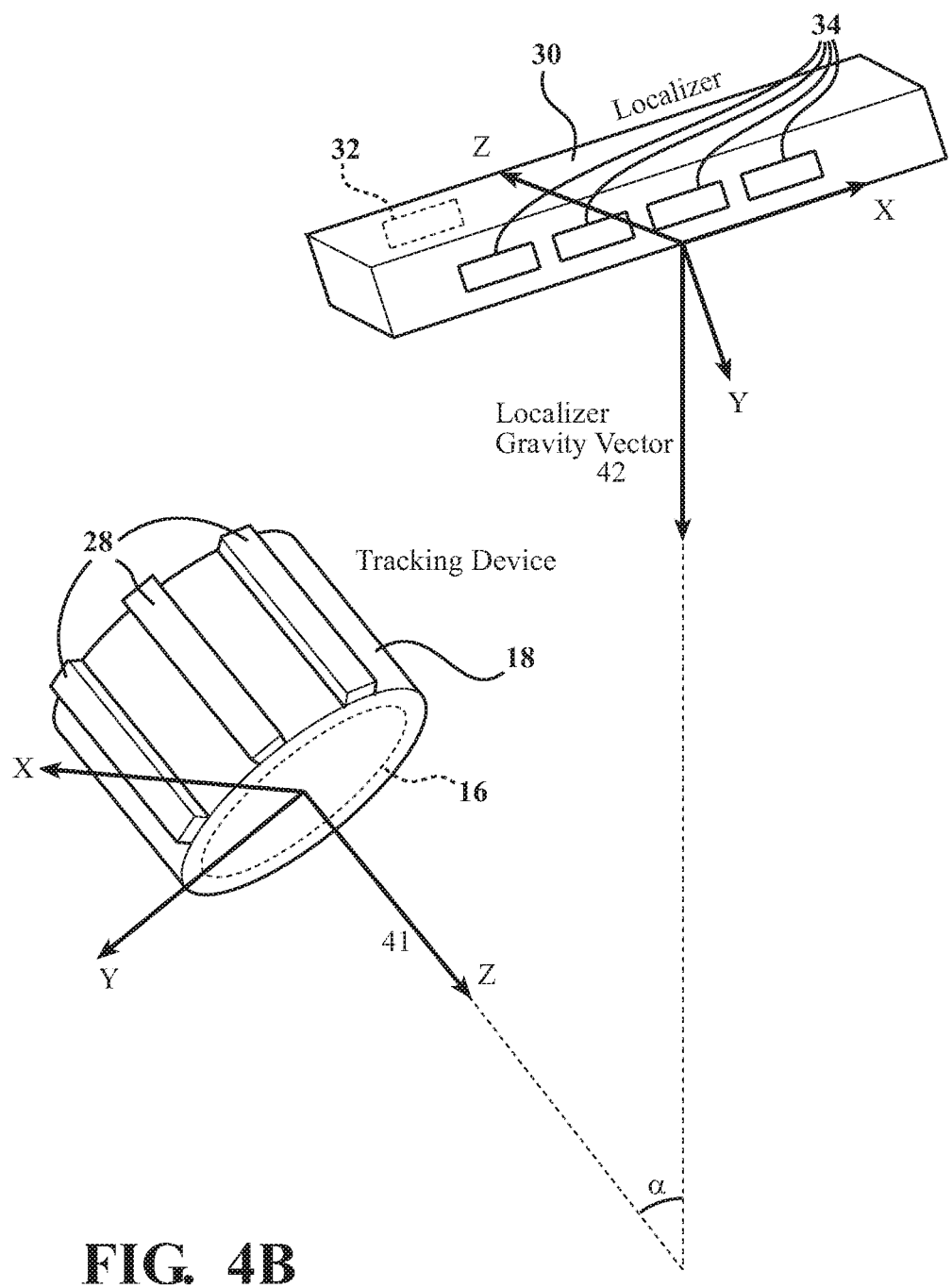
FIG. 4B illustrates the tracking device and localizer with the optical tracking sensor and gravity vector sensor, and the associated angle vectors in a second representative position.
Figure 5:
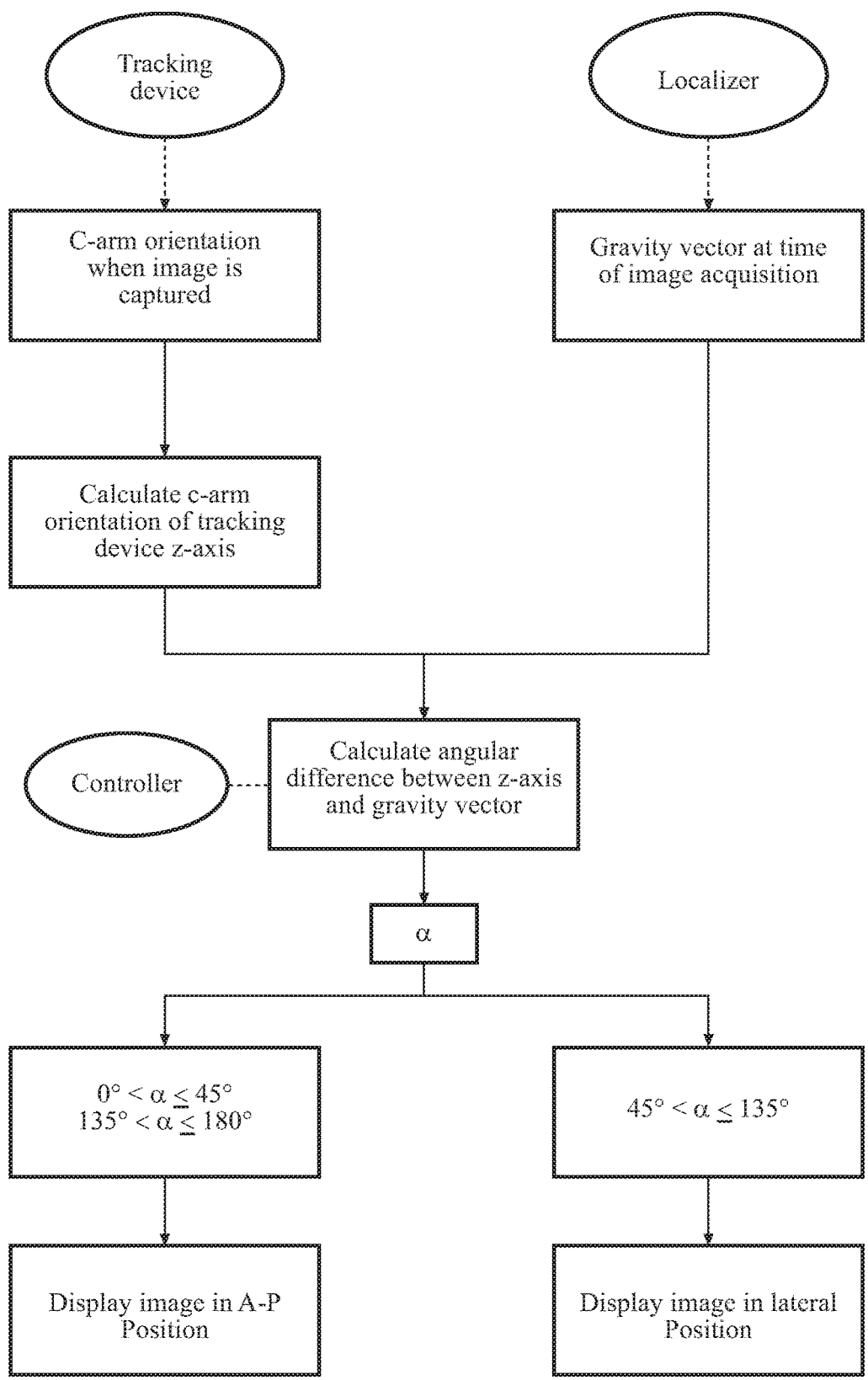
FIG. 5 shows the process by which the surgical navigation system determines which view to display based on the determined angle.

Turning to FIGS. 4A, 4B, and 5, the localizer 30 is shown with tracking sensors 34 and gravity vector sensor 32. The tracking sensors 34 are configured to optically track tracking elements 28 on the image tracking device 18 on the imaging portion 16 of the C-arm 14. The localizer 30 sends the relative position of the image tracking device 18 and the gravity vector data from the gravity vector sensor 32 to the computer processor 38. The computer processor 38 then calculates an image vector 41 relative the gravity vector 42. The gravity vector sensor 32 may be within the localizer 30, however, it is contemplated that the gravity vector sensor 32 may be located separate of the localizer 30. The computer processor 38 analyzes the pose of the image tracking device 18 as determined by the tracking sensors 34 of the localizer 30 relative to the gravity vector 42 as determined by the gravity vector sensor 32 and calculates the determined angle (α) 44. The computer processor 38 uses the determined angle 44 to ascertain which pose the imaging portion 16 of the C-arm 14 was in when the x-ray image was taken.

The computer processor 38 includes a memory coupled with the computer processor. The memory is configured to store a plurality of predefined range of angles, with each predefined range of angles being exclusive. In this example, the memory includes at least a first predefined range of angles and a second predefined range of angles exclusive from the first predefined range of angles.

In one example, the computer processor 38 determines between two poses which the imaging portion 16 of the C-arm 14 can be in when an x-ray image is taken. The computer processor 38 determines whether the imaging portion 16 of the image tracking device 18 is in the A-P pose or the lateral pose. The A-P pose is associated with the angular difference between the image vector 41 of the image tracking device 18 and the gravity vector 42 calculated by the computer processor 38 for a determined angle 44 of $0°<\alpha\leq45°$ and $135°<\alpha\leq180°$. The lateral pose is associated with the angular difference between the image vector 41 of the tracking device 18 and the gravity vector 42 calculated by the computer processor 38 for a determined angle 44 of $45°<\alpha\leq135°$.

Once the computer processor 38 calculates and determines the corresponding pose of the x-ray imaging device 16, the computer processor may automatically display the x-ray image 52, 54 on the display 50 with its associated image identifier. When the x-ray imaging device acquires several x-ray images which fall within the same predefined range of angles, the computer processor automatically updates the x-ray image displayed with the most current image acquired. For example, the x-ray imaging device takes a first A-P image and a second A-P image after the first A-P image, the second A-P image will replace the first A-P image on the display automatically. This may improve workflow between preoperative planning and intraoperative imaging since an operator will not have to signal the surgical navigation system which image(s) is going to be updated with another x-ray image.

The surgical navigation system 10 also provides for a visual representation of a surgical instrument 24. The visual representation of the surgical instrument 24 is overlaid onto the displayed image 52, 54, showing the visual representation of the surgical instrument appearing from one of at least two different perspectives based on the image identifier. The display is configured to display the x-ray image 52, 54 with image identifiers 56, 58 corresponding to the angular position at which the x-ray image was acquired.

The present disclosure is not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A surgical navigation system for use with an x-ray imaging device configured to acquire an x-ray image of an anatomical structure at one of a plurality of angular positions relative to a direction toward center of Earth gravity, the system comprising:
   a localizer unit comprising a tracking sensor and a gravity vector sensor, the tracking sensor and the gravity vector sensor mounted to the localizer unit, wherein the gravity vector sensor is configured to detect the direction toward center of Earth gravity regardless of an orientation of the tracking sensor;
   a tracking device configured to be coupled to the x-ray imaging device so as to be movable with movement of the x-ray imaging device between the plurality of angular positions, the tracking device comprising a tracking element detectable by the tracking sensor;
   a computer processor operatively coupled to the localizer unit; and
   a display coupled to the computer processor, wherein the computer processor configured to implement an imaging routine comprising:
      receiving tracking data from the tracking sensor and a gravity vector from the gravity vector sensor;
      generating an image vector based on the tracking data with the image vector being indicative of the one of the plurality of angular positions at which the x-ray image was acquired;
      determining an angle between the image vector and the gravity vector; and
      assigning a first image identifier to the x-ray image based on the determined angle, the first image identifier configured to provide an indication of the one of the plurality of angular position at which the x-ray image was acquired,
      wherein the system is configured to display the x-ray image with the first image identifier;
      updating the x-ray image on the display with a second x-ray image on the display responsive to the second x-ray image being assigned a second image identifier the same as the first image identifier, the second image identifier based on a second determined angle between a second image vector being indicative of one of the plurality of angular positions at which the second x-ray image was acquired, and the gravity vector.

2. The system of claim 1, further comprising memory coupled to the computer processor and configured to store a first predefined range of angles and a second predefined range of angles exclusive from the first predefined range of angles, wherein the imaging routine further comprises:
   receiving the first and second predefined ranges of angles from the memory;
   determining whether the determined angle is within the first predefined range of angles or the second predefined range of angles; and
   assigning the first image identifier to the x-ray image when the determined angle is within the first predefined range of angles and not within the second predefined range of angles.

3. The system of claim 2, wherein the first predefined range of angles is greater than 450 to less than or equal to 1350, and wherein the second predefined range of angles is greater than 00 to less than or equal to 450, and greater than 1350 to less than or equal to 1800.

4. The system of claim 3, wherein the first image identifier is a lateral image identifier configured to be displayed along with the x-ray image to provide the indication that the x-ray image is a lateral x-ray image of the anatomical structure.

5. The system of claim 1, wherein the computer processor is configured to display a visual representation of a surgical instrument onto the x-ray image on the display with the visual representation appearing from one of at least two different perspectives based on the image identifier.

6. A method for acquiring x-ray images of an anatomical structure with a C-arm imaging device and identifying the x-ray images on a display, wherein a navigation system is provided and includes a localizer unit including a tracking sensor connected to the localizer unit and a gravity vector sensor mounted to the localizer unit and configured to detect a direction toward center of Earth gravity regardless of an orientation of the tracking sensor, a tracking device coupled to the C-arm imaging device and including a tracking element detectable by the tracking sensor, and a computer processor, said method comprising: acquiring a first x-ray image with the C-arm imaging device at a first angular position, wherein the tracking sensor detects a first pose of the tracking device as the first x-ray image is acquired; generating with the computer processor a first image vector based on the first pose of the tracking device; generating a gravity vector based on the gravity vector sensor; determining with the computer processor a first angle between the first image vector and the gravity vector; assigning with the computer processor a first image identifier to the first x-ray image based on the first determined angle; displaying the first x-ray image on the display; acquiring a second x-ray image with the C-arm imaging device at a second angular position different than the first angular position, wherein the tracking sensor detects a second pose of the tracking device as the second x-ray image is acquired; generating with the computer processor a second image vector based on the second pose of the tracking device; determining with the computer processor a second angle between the second image vector and the gravity vector; assigning with the computer processor a second image identifier to the second x-ray image based on the second determined angle;

updating the x-ray image on the display with the second x-ray image on the display responsive to the second x-ray image being assigned a second image identifier the same as the first image identifier.

7. The method of claim 6, wherein the tracking element of the tracking device is a first tracking element, said method further comprising: providing a surgical instrument, and a second tracking element coupled to the surgical instrument; tracking a pose of the surgical instrument by detecting the second tracking element with the tracking sensor; and overlaying a visual representation of the surgical instrument onto at least one of the first and second x-ray images on the display with the visual representation appearing from one of at least two different perspectives based on the first and second image identifiers.

8. The method of claim 6, wherein the first image identifier corresponds with the first x-ray image being one of an anterior-posterior (A-P) x-ray image and a lateral x-ray image of the anatomical structure, and wherein the second image identifier corresponds with the second x-ray image being one of another A-P x-ray image and another lateral x-ray image of the anatomical structure.

9. The method of claim 6, wherein the navigation system includes memory configured to store a first predefined range of angles and a second predefined range of angles exclusive from the first predefined range of angles, said method further comprising: determining with the computer processor whether the first determined angle is within the first predefined range of angles; assigning the first image identifier to the first x-ray image when the first determined angle is within the first predefined range of angles; determining with the computer processor whether the second determined angle is within the second predefined range of angles; and assigning the second image identifier to the second x-ray image when the second determined angle is within the second predefined range of angles.

10. The method of claim 9, wherein the first predefined range of angles is greater than 450 to less than or equal to 1350, and wherein the second predefined range of angles is greater than 00 to less than or equal to 450, and greater than 1350 to less than or equal to 1800.

11. The method of claim 6, wherein the step of displaying the first x-ray image on the display is performed after the step of assigning the first image identifier and prior to the step of acquiring the second x-ray image.

* * * * *

UNITED STATES PATENT AND TRADEMARK OFFICE
CERTIFICATE OF CORRECTION

PATENT NO. : 11,871,998 B2
APPLICATION NO. : 16/706138
DATED : January 16, 2024
INVENTOR(S) : Patrick Hornecker et al.

It is certified that error appears in the above-identified patent and that said Letters Patent is hereby corrected as shown below:

In the Claims

Column 12, Line 45, Claim 3:
Please replace "greater than 450 to less than or equal to 1350" with -- "greater than 45° to less than or equal to 135°" --

Column 12, Line 47, Claim 3:
Please replace "greater than 00 to less than or equal to 450, and greater than 1350 to less than or equal to 1800" with -- greater than 0° to less than or equal to 45°, and greater than 135° to less than or equal to 180° --

Column 14, Line 26, Claim 10:
Please replace "greater than 450 to less than or equal to 1350" with -- greater than 45° to less than or equal to 135° --

Column 14, Line 28, Claim 10:
Please replace "greater than 00 to less than or equal to 450, and greater than 1350 to less than or equal to 1800" with -- greater than 0° to less than or equal to 45°, and greater than 135° to less than or equal to 180° --

Signed and Sealed this
Eighteenth Day of June, 2024

Katherine Kelly Vidal
*Director of the United States Patent and Trademark Office*